United States Patent [19]

Sturm et al.

[11] Patent Number: 4,644,166

[45] Date of Patent: Feb. 17, 1987

[54] SENSOR FOR TESTING LIGHT AND WEATHER RESISTANCE OF SAMPLES

[75] Inventors: Walter Sturm, Hanau; Helmut Becker, Limeshain; Jürgen Witt, Hainburg; Werner Fritz, Steinau-Sarrod; Ursula Eysholt, Hanau, all of Fed. Rep. of Germany

[73] Assignee: W. C. Heraeus GmbH, Hanau, Fed. Rep. of Germany

[21] Appl. No.: 862,206

[22] Filed: May 12, 1986

Related U.S. Application Data

[63] Continuation of Ser. No. 587,826, Mar. 9, 1984, abandoned.

[30] Foreign Application Priority Data

Mar. 24, 1983 [DE] Fed. Rep. of Germany ... 8308709[U]

[51] Int. Cl.$^4$ .............................................. G01N 17/00
[52] U.S. Cl. .................. 250/372; 73/150 R; 356/51
[58] Field of Search ............... 250/372, 373, 239, 226; 356/407, 51; 73/150 R

[56] References Cited

U.S. PATENT DOCUMENTS

| Re. 29,833 | 11/1978 | Mlavsky ................... 357/20 |
| 3,686,940 | 8/1972 | Kockott ................... 73/150 |
| 3,838,282 | 9/1974 | Harris ..................... 250/372 |
| 3,973,118 | 8/1976 | LaMontagne ............... 250/239 |
| 4,214,835 | 7/1980 | Roos ...................... 356/328 |
| 4,391,522 | 7/1983 | Schmid et al. ............. 356/328 |
| 4,428,050 | 1/1984 | Pellegrino et al. ......... 250/372 |

FOREIGN PATENT DOCUMENTS 1150229 6/1963 Fed. Rep. of Germany .

OTHER PUBLICATIONS

"Ultra-Violet Measuring Instrument for all Weathering Tests", trade brochure, Heraeus GmbH, Fed. Rep. of Germany, 1-83.

Primary Examiner—Carolyn E. Fields
Attorney, Agent, or Firm—Frishauf, Holtz, Goodman & Woodward

[57] ABSTRACT

A sensor for use in testing the effect on materials of irradiation and weathering uses solar cells (10) to provide power and uses a transmitter (3) to continuously read out its measurements without interrupting the testing process. The sensor features a number of receptor cells (2) for various spectral ranges and a temperature sensor (17), whose measurements are multiplexed and transmitted under the control of a control logic 18. The receptor cells (2), the photo cells (10) and the electronics (16) are all contained in a preferably cylindrical quartz glass tube (4). The self-contained nature of the sensor and the continuous, immediate read-out of measurements eliminate external wiring requirements and speed up the testing process.

14 Claims, 4 Drawing Figures

SENSOR FOR TESTING LIGHT AND WEATHER RESISTANCE OF SAMPLES

This is a continuation of application Ser. No. 587,826, filed Mar. 9, 1984, now abandoned.

Cross reference to related application, assigned to the assignee of the present application, the disclosure of which is hereby incorporated by reference: U.S. Ser. No. 587,500, filed Mar. 9, 1984, STURM et al, "LIGHT AND WEATHER RESISTANCE SENSING SYSTEM WITH A SENSED SIGNAL TRANSMISSION CHANNEL" now U.S. Pat. No. 4,618,776, issued Oct. 21, 1986. (claiming priority of German Application P. 33 10 631.2-52 of Mar. 24, 1983).

The present invention relates generally to testers for measuring the effect of light and weather on samples of various materials, and more particularly to a revolvable sensor placed in the simulation or test chamber with the samples, whose power supply and signal transmission means do not require external wiring.

BACKGROUND

A sensor, which can be placed in a testing device in the same manner as a sample carrier and exposed to radiation from lamps, is known from sales leaflet D 310 608/2 C5.82/N Ku of the Original Hanau division of the W. C. Heraeus GmbH firm. This sensor is powered by batteries and converts the radiation of a predetermined specific spectral range into corresponding electrical signals and stores away the radiation dose. Upon completion of the test, one can display the desired values by means of a measuring device to be connected to the sensor.

THE INVENTION

It is an object to provide a sensor with an independent power supply which can simultaneously measure various spectral ranges. Another object is to enable continuous measurement during the course of testing the samples.

Briefly, the sensor includes a cylindrical housing translucent to the radiation from lamps to be measured, in which are arranged multiple receptor cells for various respective spectral ranges and a radio transmitter for wireless transmission of signals representing the measurements. Preferably, the housing comprises a quartz glass tube, having at its two ends detachable metal stoppers. The stoppers are preferably provided with gaskets or other packing material where they contact the tube and are connected to each other by means of a threaded central connecting rod. The quartz glass tube preferably includes on its inner surface an infrared absorbing film which, however, transmits sufficient heat waves from the lamps to drive solar cells.

Advantageously, the housing includes at one of its end regions solar cells providing electrical power and a number of receptor cells arranged next to each other along the longitudinal direction of the housing. The sensor receives the radiation given off by lamps and converts the radiation into electrical signals by means of receptor cells. Power is supplied by the solar cells by conversion of the same radiation. The solar cells may also be arranged in the longitudinal direction of the housing in the same row as the receptor cells. Preferably the sensor includes at least one receptor cell for the spectral range of from 300 to 400 nanometers (ultraviolet region) and at least one receptor cell for the spectral range of from 300 to 800 nm (ultraviolet and visible rays). It is desirable to provide four receptor cells for measurement of the radiation in the ultraviolet region, of which one each covers the wave length ranges from 300 to 320 nm, from 330 to 350 nm, from 355 to 375 nm, and from 380 to 400 nm, respectively, while a further receptor cell covers the spectral range from 300 to 400 nm, and yet another receptor cells covers the entire spectral range from 300 to 800 nm. The receptor cells for the four ultraviolet spectrum divisions include an interference filter, an apertured partition, and a diffusing lens in front of a photo cell, and the remaining receptor cells have an interference filter and two diffusing lenses of varying thicknesses in front of a photo cell. The housing preferably includes a connecting terminal for a temperature measurement sensor. The receptor cells are interrogated, producing signals, corresponding to the radiation, whih are combined in the multiplexer and subsequently transmitted serially by frequency modulation in the transmitter.

The sensor of the present invention has the advantage that an immediate measurement can be obtained in the plane of the samples during the testing of the samples and, therefore, one can compare the measurements made in various weathering devices and weather installations.

DRAWINGS

DETAILED DESCRIPTION

Figure 1:
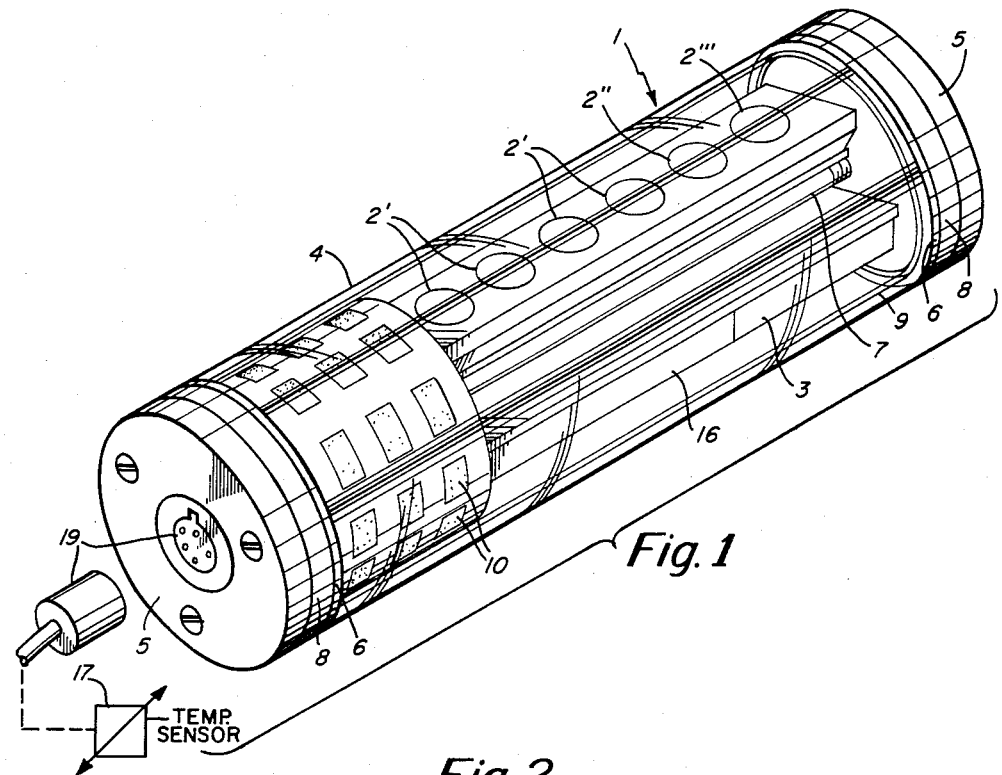
FIG. 1 is a perspective view of the sensor.

FIG. 1 shows the sensor of the present invention with its housing 1, comprising a quartz glass tube 4 having at each of its ends a metal stopper 5 with a circumferential gasket, packing or other seal 6. Within the housing are a row of receptor cells generally given reference numerals 2', 2", 2''' disposed along the longitudinal direction of the housing, solar cells 10 and accompanying electronics 16. In addition, a plug socket is provided on the housing as part of a connection 19 for a temperature measurement sensor 17, for example Pt 100.

Figure 2:
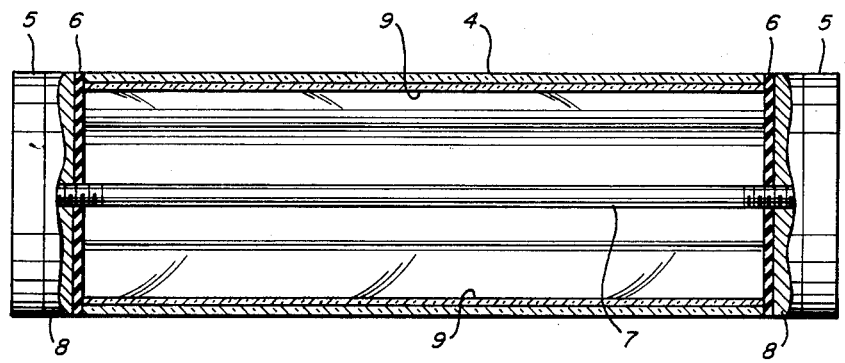
FIG. 2 is a longitudinal cross section through the sensor housing.

FIG. 2 shows in cross section the components of the housing, including the quartz glass tube 4 with its infrared radiation limiting film or layer 9 and the two stoppers 5 which are preferably of metal and comprise two plates or panels 8 connected to each other by a screw connection 7 such as a threaded rod disposed along the longitudinal axis of the housing. Between the plates 8, connected to each other by the screw connector 7 and the quartz glass tube 4, is a gasket 6, preferably of rubber, which is pressed against the rim of the quartz glass tube 4 as the plates are screwed toward each other on the threaded rod 7.

Figure 3:
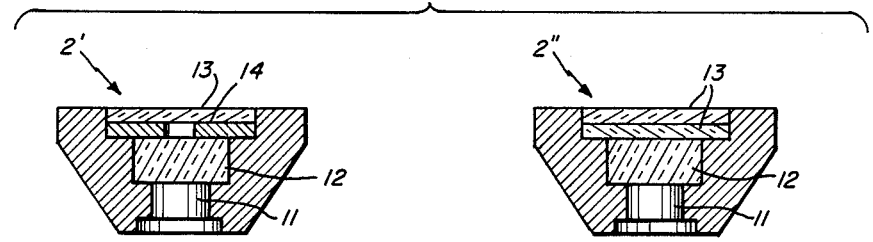
FIG. 3 shows in cross section two different receptor cell constructions.

As shown in FIG. 3, the receptor cells 2' for the four ultraviolet ranges comprise a photo cell, in front of which are arranged an interference filter 12, an apertured partition 14 and a diffusing lens 13 for cosine correction. The receptor cell 2" for the entire range and 2''' for the spectral range covering both ultraviolet and visible light each comprise a photo cell 11, an interference filter 12 and two diffusing lenses 13.

Figure 4:
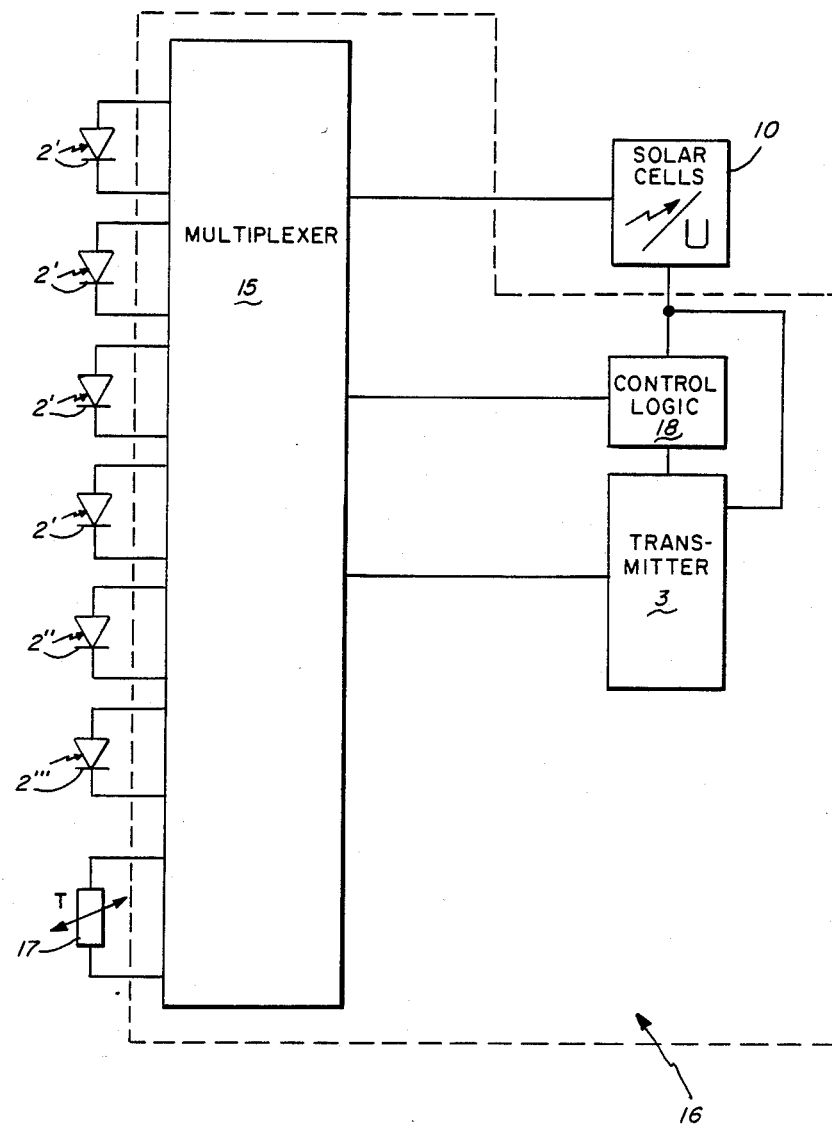
FIG. 4 is a schematic block diagram of the circuit within the sensor.

FIG. 4 illustrates schematically the electronic circuit 16 of the sensor of the present invention which includes the individual receptor cells, the temperature sensor 17, the multiplexer 15, transmitter 3 and the control logic 18. The receptor cells 2 and the temperature sensor 17 are connected to the multiplexer 15, which is connected to the transmitter 3 for the broadcast of the measurement signals, to the solar cells 10 for power supply purposes, and to the control logic 18 for control of the data transmission.

A suitable multiplexer is Model MC 14051 from the firm Motorola Semiconductor Products Inc., USA.

A suitable control logic is a digital CMOS circuit for sequencing signals for transmission comprising different electronic components of the MC 14 . . . series from the firm Motorola Semiconductor Products Inc., USA.

The solar cells used are preferably the Model SSC-8-1010H from the firm KODENSHI Ltd., Kyoto, Japan, and under normal testing conditions will produce a current of at least 23 milliamperes at 6.5 volts. The model numbers and manufacturers of the preferred photo cells 2', 2" and 2''' are, respectively, as follows:

Manufacture: Hamamatsu, TVCO, Ltd., 1126, ICHINO-CHO, Hamamatsu, Japan
cells 2' and cells 2": Type G1126-02
cell 2''': Type S1226-5BQ

We claim:

1. A compact, revolvable, self-contained and electrically self-sufficient simulated-solar-radiation and temperature measuring sensor adapted for use in a weather resistance testing chamber, comprising, in accordance with the invention, a sealed housing (1) transparent to the simulated solar radiation to be measured, a plurality of receptor cells (2', 2", 2''') disposed in said housing, said receptor cells each comprising an interference filter (12) and at least one diffusing lens (13) in front of a photocell (11) and being responsive to differing wavelength ranges of incident radiation and generating signals representing radiation received, a multiplexer (15) connected to said receptor cells and sequencing said signals for serial transmission, a plurality of solar cells (10) disposed in said housing and generating, entirely from incident simulated solar radiation, sufficient electrical power for generation and transmission of said signals, and a single radio transmitter (3) connected to said multiplexer (15) for radio transmission of said signals, during revolution of said sensor, to a stationary receiver.

2. The sensor of claim 1, wherein said housing (1) comprises a cylindrical quartz glass tube (4) having two ends, a circular detachable stopper (5) at each of said ends of said tube (4), means (7) for adjustably securing said stoppers (5) in spaced relation to each other, and gasket means (6) for forming a seal between each stopper (5) and a circular peripheral edge of an end of said tube (4).

3. The sensor of claim 2, wherein said quartz glass tube (4) has an inner surface, said inner surface bearing a film (9) which limits transmission of infrared radiation.

4. The sensor of claim 2, wherein said securing means (7) comprises a threaded rod which screws into each of said stoppers.

5. The sensor of claim 2, wherein a plurality of said receptor cells (2) are arranged in a row parallel to the longitudinal axis of said cylindrical quartz glass tube (4).

6. The sensor of claim 5, wherein said solar cells are arranged in a row with said receptor cells.

7. The sensor of claim 1, wherein at least one (2") of said receptor cells (2) is responsive to radiation in the ultraviolet wavelengths from 300 to 400 nm and at least one (2''') of said receptor cells is responsive to ultraviolet and visible radiation in the spectral range from 300 to 800 nm.

8. The sensor of claim 7, wherein four (2') of said receptor cells are respectively responsive to radiation in partial ultraviolet wavelength ranges from 300 to 320 nm, 330 to 350 nm, 355 to 375 nm, and 380 to 400 nm, a further receptor cell (2") is responsive to the complete ultraviolet spectral range from 300 to 400 nm, and yet another receptor cell (2''') is responsive to the entire ultraviolet and visible spectral range from 300 to 800 nm.

9. The sensor of claim 8, wherein said receptor cells (2') for the four partial ultraviolet spectral ranges comprise an interference filter (12), an apertured partition (14) and a diffusing lens (13) disposed in front of a photo cell (11), and the remainder of said receptor cells (2", 2''') each comprise an interference filter (12) and two diffusing lenses (13) in front of a photo cell (11).

10. The sensor of claim 1, further comprising a connection terminal (19) on said housing (1) for a temperature measuring device.

11. The sensor of claim 1, further comprising control logic (18) connected to and regulating said multiplexer (15) and said transmission means (3).

12. The sensor of claim 11, wherein said control logic is a digital CMOS circuit.

13. The sensor of claim 1, further comprising means (19) on said housing for connecting said sensor to an external temperature sensor (17).

14. The sensor of claim 1, wherein said multiplexer is a Motorola Model MC 14051.

* * * * *